(12) United States Patent
Ali et al.

(10) Patent No.: US 8,530,521 B2
(45) Date of Patent: Sep. 10, 2013

(54) NITROOXY CYCLOALKANE DERIVATIVES

(75) Inventors: Amjad Ali, Freehold, NJ (US); Robert K. Baker, Cranford, NJ (US); Kathleen M. Rupprecht, Cranford, NJ (US); Michael Man-Chu Lo, Edison, NJ (US); Brent Whitehead, Morristown, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 117 days.

(21) Appl. No.: 13/130,473

(22) PCT Filed: Jul. 27, 2009

(86) PCT No.: PCT/US2009/051794
§ 371 (c)(1),
(2), (4) Date: May 20, 2011

(87) PCT Pub. No.: WO2010/062415
PCT Pub. Date: Jun. 3, 2010

(65) Prior Publication Data
US 2011/0230532 A1    Sep. 22, 2011

Related U.S. Application Data

(60) Provisional application No. 61/200,310, filed on Nov. 26, 2008.

(51) Int. Cl.
*A61K 31/16*      (2006.01)
*C07C 381/00*     (2006.01)
*C07C 303/00*     (2006.01)
*C07C 233/00*     (2006.01)

(52) U.S. Cl.
USPC ............. 514/616; 558/440; 564/80; 564/164; 564/201; 564/210

(58) Field of Classification Search
USPC ........................................ 514/616; 564/160
See application file for complete search history.

(56) References Cited

U.S. PATENT DOCUMENTS

| 5,411,989 A | * | 5/1995 | Michel et al. ................. 514/616 |
| 2002/0183366 A1 | | 12/2002 | Garvey et al. |
| 2005/0065194 A1 | * | 3/2005 | Shankar et al. ............... 514/362 |

OTHER PUBLICATIONS

Patani et al., Chem Rev, 1996, vol. 96 (8), especially p. 3149.*
PCT Search Report for International Patent Application No. PCT/US09/51794; Completed—Sep. 5, 2009; by US Searching Authority; Performed by Authorized officer—Lee W. Young.

* cited by examiner

*Primary Examiner* — Susannah Chung
(74) *Attorney, Agent, or Firm* — Richard S. Parr; Catherine D. Fitch

(57) ABSTRACT

A compound having the structure wherein Y is selected from the group consisting of —C(O)OR², —C(O)NHR⁸, —C(CH₂)₁₋₂OR3, OH, and or a pharmaceutically acceptable salt thereof, and methods of using the compounds for treating hypertension.

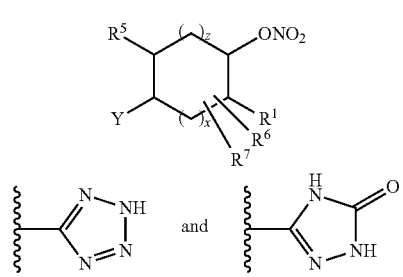

12 Claims, No Drawings

NITROOXY CYCLOALKANE DERIVATIVES

CROSS REFERENCE TO RELATED APPLICATIONS

This application is a U.S. National Phase application under 35 U.S.C.§371 of PCT Application No. PCT/US09/051794 filed Jul. 27, 2009, which claims priority under 35 U.S.C.§119(e) from U.S. Provisional Application No. 61/200,310 filed on Nov. 26, 2008.

BACKGROUND OF THE INVENTION

US 2005137191 describes nitrate ester compounds, e.g., 1,2-dichloro-4-(2-methyl-butyldisulfanyl)-benzene, useful for preventing or mitigating tissue and/or cellular damage associated with aging, septic shock, ulcers, gastritis, ulcerative colitis and Crohn's disease. US 2005065194 describes use of an endothelial gene differentiation receptor modulator such as 1-(2-ethoxyphenyl)-3-(hydroxyphenylamino)-pyrrolidine-2,5-dione, to modulate receptor-mediated biological activity such as cell proliferation stimulated by lysophosphatidic acid leading to ovarian cancer and other forms of cancer, and to treat conditions such as cancer, cardiovascular disease, ischemia, and atherosclerosis. WO 9746521 describes aliphatic nitrate esters useful for treating neurological conditions, especially Parkinson's, Alzheimer's and Huntington's disease.

The present invention relates to novel nitrooxy cycloalkane derivatives, such as nitrooxy cyclopentane carboxylic acid derivatives, useful as antihypertensive agents.

SUMMARY OF THE INVENTION

The present invention includes nitrooxy cycloalkane derivatives, including various pharmaceutically acceptable salts and hydrates of these forms, and pharmaceutical formulations for controlled and sustained delivery of these forms to a patient.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

The invention is a compound of formula I:

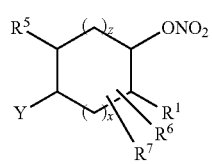

or a pharmaceutically acceptable salt thereof, wherein
x is an integer selected from the group consisting of 1, 2 and 3;
z is 0 or 1;
Y is selected from the group consisting of —C(O)OR$^2$, —C(O)NHR$^8$, —(CH$_2$)$_{1-2}$OR$^3$, —OH,

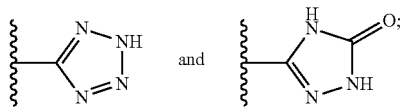 [SMILES: *c1nn[nH]n1 ; *c1n[nH]c(=O)[nH]1]

R$^1$ is selected from the group consisting of
1) —ONO$_2$,
2) —O—CH$_3$,
3) —O-aryl,
4) —O-heteroaryl,
5) —O—C$_{3-8}$ cycloalkyl,
6) -aryl,
7) -heteroaryl,
8) —C$_{3-8}$ cycloalkyl, and
9) halogen;
R$^2$ is selected from the group consisting of
1) hydrogen
2) —C$_{1-6}$ alkyl,
3) -aryl,
4) —CH$_2$OC(O)C$_{1-6}$ alkyl, and
5) —(CH$_2$)$_{1-2}$N$^+$(R$^9$)$_3$;
R$^3$ is selected from the group consisting of
1) hydrogen,
2) —C(O)C$_{1-6}$ alkyl, and
3) —P(O)(OH)$_2$,
R$^5$ is selected from the group consisting of hydrogen and —OH;
R$^6$ is selected from the group consisting of hydrogen and —OH;
R$^7$ is absent or, when x is 2 or 3, is selected from the group consisting of hydrogen and —OH;
R$^8$ is selected from the group consisting of hydrogen, —CH(R$^{10}$)COOH,

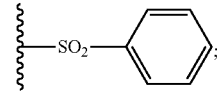 [SMILES: *S(=O)(=O)c1ccccc1]

R$^9$ in each instance in which it occurs, is independently C$_{1-3}$ alkyl; and
R$^{10}$ is straight or branched C$_{1-6}$ alkyl,
wherein alkyl is unsubstituted or substituted on any carbon atom with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—, (C$_1$-C$_6$ alkyl)S(O)$_{0-2}$(C$_1$-C$_6$ alkyl)-, HS(O)$_{0-2}$(C$_1$-C$_6$ alkyl)-, (C$_0$-C$_6$ alkyl)C(O)NH—, H$_2$N—C(NH)—, —O(C$_1$-C$_6$ alkyl)CF$_3$, HC(O)—, (C$_1$-C$_6$ alkyl)C(O)—, HOC(O)—, (C$_1$-C$_6$ alkyl)OC(O)—, —HO(C$_1$-C$_6$ alkyl)-, (C$_1$-C$_6$ alkyl)O(C$_1$-C$_6$ alkyl)-, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$—, HOC(O)NH—, (C$_1$-C$_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, wherein aryl is unsubstituted or substituted on any carbon atom with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, ($C_1$-$C_6$ alkyl)S(O)$_{0-2}$($C_1$-$C_6$ alkyl)—, —HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl), ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, wherein cycloalkyl unsubstituted or substituted on any carbon atom with unsubstituted, or substituted with 1-3 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, and wherein heteroaryl is a 5 or 6-membered aromatic ring containing 1, 2, 3 or 4 heteroatoms, independently selected from N, O or S, which is unsubstituted, or substituted with 1 substituent on any one or more carbon atoms, with halogen, $C_1$-$C_{20}$ alkyl, $CF_3$, $NH_2$, alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—($C_1$-$C_6$ alkyl)S(O)$_{0-2}$($C_1$-$C_6$ HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ HO($C_1$-$C_6$ alkyl)-, ($C_1$-$C_6$ alkyl)O—, ($C_1$-$C_6$ alkyl)C(O)$_{1-2}$($C_1$-$C_6$ HC(O)$_{1-2}$($C_1$-$C_6$ ($C_1$-$C_6$ alkyl)C(O)$_{1-2}$, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_{1-6}$ alkyl, —C(O)NH$_2$, —$C_1$-$C_6$ alkylC(O)NH$_2$, or —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, or aryl.

In one embodiment of the invention, the compound has the formula Ia

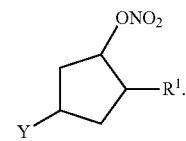

Ia

In another embodiment of the invention, $R^1$ is selected from the group consisting of
1) —$ONO_2$,
2) —O—$CH_3$,
3) —O-aryl,
4) —O-heteroaryl,
5) —O—$C_{3-8}$ cycloalkyl, and
6) halogen.

In another embodiment of the invention, the compound has the formula Ia

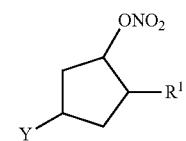

Ia

Y is selected from the group consisting of —C(O)O$R^2$, —$CH_2$O$R^3$, or —C(O)NH$R^8$;

$R^1$ is selected from the group consisting of
1) —O—$NO_2$,
2) —O—$CH_3$,
3) —O-aryl,
4) —O-heteroaryl,
5) —O—$C_{3-8}$ cycloalkyl, and
6) halogen;

$R^2$ is selected from the group consisting of
1) hydrogen
2) —$C_{1-6}$ alkyl,
3) -aryl,
4) —$CH_2$OC(O)$C_{1-6}$ alkyl, and
5) —($CH_2$)$_2$$N^+$($CH_3$)$_3$;

$R^3$ is selected from the group consisting of
1) hydrogen,
2) —C(O)$C_{1-6}$ alkyl, and
3) —P(O)(OH)$_2$.

In another embodiment of the invention, Y is selected from the group consisting of —C(O)O$R^2$, —C(O)NH$_2$, —($CH_2$)$_{1-2}$ OH, —OH, —C(O)NHCH(CH($CH_3$)$_2$)COOH,

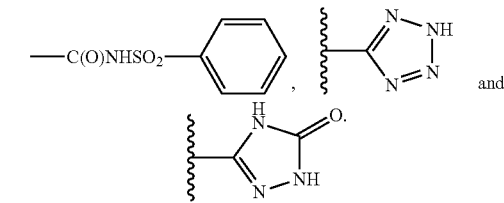

and

In another embodiment of the invention, $R^2$ is hydrogen, —$(CH_2)_2N^+(CH_3)_3$ or —$CH_3$.

In another embodiment of the invention, $R^1$ is selected from the group consisting of —O—$CH_3$, —$ONO_2$ and F.

In another embodiment of the invention, $R^1$ is —$OCH_3$.

In another embodiment of the invention, Y is —C(O)OH or —C(O)$OCH_3$. In another embodiment of the invention, Y is —C(O)OH or —C(O)$OCH_3$ and $R^1$ is —$OCH_3$.

In another embodiment, $R^5$ and $R^6$ are hydrogen, and x is 1 and z is 0.

In another embodiment of the invention, the compound has the formula

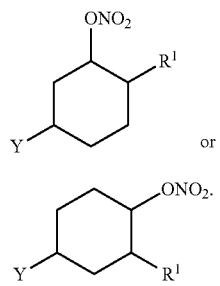

In another embodiment of the invention, the compound is selected from the group consisting of
(+)-(1S, 3R,4R)-3-Methoxy-4-(nitrooxy)cyclopentanecarboxylic acid,
(1R,3R,4R)-3-methoxy-4-(nitrooxy)cyclopentanecarboxylic acid,
(1S,3S,4R)-3-methoxy-4-(nitrooxy)cyclopentanecarboxylic acid,
(1R,3S,4R)-3-methoxy-4-(nitrooxy)cyclopentanecarboxylic acid,
(1R,3R,4R)-3-fluoro-4-(nitrooxy)cyclopentanecarboxylic acid,
2-Hydroxy-3-(2-hydroxyethyl)-5-methoxycyclopentyl nitrate,
4-(Hydroxymethyl)cyclopentane-1,2-diyl dinitrate,
(1R,2S,4r)-4-Hydroxycyclopentane-1,2-diyl dinitrate,
(1R,2S,4s)-4-Hydroxycyclopentane-1,2-diyl dinitrate,
(1S,2S,4R)-4-carbamoyl-2-methoxycyclopentyl nitrate,
(1S,2S,4R)-2-methoxy-4-(1H-tetrazol-5-yl)cyclopentyl nitrate,
(1R,2R,4S)-2-methoxy-4-(1H-tetrazol-5-yl)cyclopentyl nitrate,
(1S,2S,4R)-2-methoxy-4-(3-oxo-3H-1,2,4-triazol-5-yl)cyclopentyl nitrate,
(1S,2S,4R)-2-methoxy-4-[(phenylsulfonyl)carbamoyl]cyclopentyl nitrate,
3-Methoxy-4-(nitrooxy)cyclopentanecarboxylic acid,
4-[(1S,3S,4S)-3-methoxy-4-nitrocyclopentyl]-N,N,N-trimethyl-4-oxobutan-1-aminium,
N-{[(1R,3S,4S)-3-methoxy-4-(nitrooxy)cyclopentyl]carbonyl}-L-valine,
(1S,3R,4R)-methyl 4-methoxy-3-(nitrooxy)cyclohexanecarboxylate,
(1S,3R,4R)-methyl 3-methoxy-4-(nitrooxy)cyclohexanecarboxylate,
(1S,3R,4R)-methyl 3-methoxy-4-(nitrooxy)cyclohexanecarboxylate,
(1S,3S,4S)-methyl 4-methoxy-3-(nitrooxy)cyclohexanecarboxylate,
(1R,3S,4S)-methyl 4-methoxy-3-(nitrooxy)cyclohexanecarboxylate,
(1R,3R,4R)-methyl 3-methoxy-4-(nitrooxy)cyclohexanecarboxylate,
(1R,3S,4S)-methyl 3-methoxy-4-(nitrooxy)cyclohexanecarboxylate, and
(1R,3R,4R)-methyl 4-methoxy-3-(nitrooxy)cyclohexanecarboxylate,
or a pharmaceutically acceptable salt thereof.

The invention also is a compound of formula I:

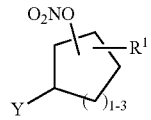

or a pharmaceutically acceptable salt thereof, wherein
Y is selected from the group consisting of —C(O)$OR^2$ and —$CH_2OR^3$;
$R^1$ is selected from the group consisting of
—$ONO_2$,
—O—$C_{1-6}$ alkyl,
—O-aryl,
—O-pheteroaryl,
—O—$C_{3-8}$ cycloalkyl,
—$C_{1-6}$ alkyl,
-aryl,
-heteroaryl, and
—$C_{3-8}$ cycloalkyl;
$R^2$ is selected from the group consisting of
hydrogen
—$C_{1-6}$ alkyl,
-aryl, and
—$CH_2OC(O)C_{1-6}$ alkyl; and
$R^3$ is selected from the group consisting of
hydrogen,
—C(O)$C_{1-6}$ alkyl, and
—P(O)(OH)$_2$,
wherein alkyl is unsubstituted or substituted on any carbon atom with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ ($C_1$-$C_6$ alkyl)C(O)—, HOC(O)—, ($C_1$-$C_6$ alkyl)OC(O)—, HO($C_1$-$C_6$ ($C_1$-$C_6$ alkyl)O ($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl,
wherein aryl is unsubstituted or substituted on any carbon atom with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2N$—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)—, HO($C_1$-$C_6$ ($C_1$-$C_6$ alkyl)

C(O)$_{1-2}$(C$_1$-C$_6$ alkyl)-, (C$_1$-C$_6$ alkyl)C(O)$_{1-2}$—, HC(O)$_{1-2}$(C$_1$-C$_6$ alkyl)-, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, wherein cycloalkyl unsubstituted or substituted on any carbon atom with unsubstituted, or substituted with 1-3 substituents on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—(C$_1$-C$_6$ alkyl OS(O)$_{0-2}$(C$_1$-C$_6$ alkyl)-, HS(O)$_{0-2}$(C$_1$-C$_6$ (C$_1$-C$_6$ alkyl)S(O)$_{0-2}$—, (C$_1$-C$_6$ alkyl)C(O)NH—, HC(O)NH—, H$_2$N—C(NH)—, —O(C$_1$-C$_6$ alkyl)CF$_3$, (C$_1$-C$_6$ alkyl)C(O)—, HC(O)—, (C$_1$-C$_6$ alkyl)OC(O)—, HOC(O)—, (C$_1$-C$_6$ alkyl)O(C$_1$-C$_6$ alkyl)-, HO(C$_1$-C$_6$ alkyl)-, (C$_1$-C$_6$ alkyl)O—, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$—, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, and wherein heteroaryl is a a 5 or 6-membered aromatic ring containing 1, 2, 3 or 4 heteroatoms, independently selected from N, O or S, which is unsubstituted, or substituted with 1 substituent on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$— (C$_1$-C$_6$ alkyl)S(O)$_{0-2}$(C$_1$-C$_6$ alkyl)-, HS(O)$_{0-2}$(C$_1$-C$_6$ alkyl)-, (C$_1$-C$_6$ alkyl)S(O)$_{0-2}$—, (C$_1$-C$_6$ alkyl)C(O)NH—, HC(O)NH—, H$_2$N—C(NH)—, O(C$_1$-C$_6$ alkyl)CF$_3$, HC(O)—, (C$_1$-C$_6$ alkyl)C(O)—, (C$_1$-C$_6$ alkyl)OC(O)—, HOC(O)—, (C$_1$-C$_6$ alkyl)O(C$_1$-C$_6$ alkyl)-, HO(C$_1$-C$_6$ alkyl)-, (C$_1$-C$_6$ alkyl)O—, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms with C$_1$-C$_{20}$ alkyl, oxo, C$_3$-C$_{10}$ cycloalkyl, C$_2$-C$_6$ alkenyl, C$_2$-C$_6$ alkynyl, aryl, —C(O)C$_{1-6}$ alkyl, —C(O)NHC$_1$-C$_6$ alkyl, —C(O) NH$_2$, —C$_1$-C$_6$ alkylC(O)NH$_2$, or —C$_1$-C$_6$ alkylOC(O)NH$_2$, or independently or additionally substituted with 1 substituent on any one or more sulfur atoms, with C$_1$-C$_{20}$ alkyl, oxo, C$_3$-C$_{10}$ cycloalkyl, C$_2$-C$_6$ alkenyl, C$_2$-C$_6$ alkynyl, or aryl.

In one embodiment of the invention, the compound has the formula Ia

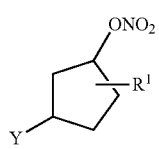

In another embodiment of the invention, R$^1$ is selected from the group consisting of
—ONO$_2$,
—O—C$_{1-6}$ alkyl,
—O-aryl,
—O-heteroaryl, and
—O—C$_{3-8}$ cycloalkyl.

In another embodiment of the invention, the compound has the formula Ia

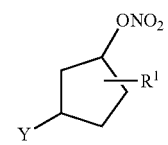

Y is selected from the group consisting of —C(O)OR$^2$ and —CH$_2$OR$^3$;
R$^1$ is selected from the group consisting of
—ONO$_2$,
—O—C$_{1-6}$ alkyl,
—O-aryl,
—O-heteroaryl, and
—O—C$_{3-8}$ cycloalkyl;
R$^2$ is selected from the group consisting of
hydrogen
—C$_{1-6}$ alkyl,
-aryl, and
—CH$_2$OC(O)C$_{1-6}$ alkyl; and
R$^3$ is selected from the group consisting of
hydrogen,
—C(O)C$_{1-6}$ alkyl, and
—P(O)(OH)$_2$.

In another embodiment of the invention, Y is —C(O)OR$^2$.
In another embodiment of the invention, R$^2$ is hydrogen.
In another embodiment of the invention, R$^1$ is C$_{1-6}$ alkyl.
In another embodiment of the invention, R$^1$ is —CH$_3$.
In another embodiment of the invention, Y is —C(O)OH and R$^1$ is C$_{1-6}$ alkyl.
In another embodiment of the invention, Y is —C(O)OH and R$^1$ is CH$_3$.

In a specific embodiment of the invention, the compound is 3-methoxy-4-(nitrooxy)cyclopentanecarboxylic acid.

Compounds of the invention can be used to treat hypertension, treat angina, improve insulin sensitivity, and provide renal protection. The compounds can be used alone or in a fixed dose combination with other antihypertensives such as, for example, angiotensin II receptor blockers, diuretics, ACE inhibitors, β-blockers, and calcium channel blockers.

Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Alkyl groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl) $S(O)_{0-2}$—, $HS(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_0$-$C_6$ alkyl)$C(O)NH$—, $H_2N$—C (NH)—, —$O(C_1$-$C_6$ alkyl)$CF_3$, HC(O)—, ($C_1$-$C_6$ alkyl)C (O)—, HOC(O)—, ($C_1$-$C_6$ alkyl)OC(O)—, HO($C_1$-$C_6$ alkyl)-, ($C_1$-$C_6$ alkyl)O($C_1$-$C_6$ ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylallcyl, cyano-aryl, cyano-aralkyl, cyano-heterocycle and cyano-heterocyclylalkyl, where such substitution results in formation of a stable compound.

The term "aryl", alone or in combination, relates to a phenyl, naphthyl or indanyl group, preferably a phenyl group. The abbreviation "Ph" represents phenyl.

Aryl groups may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $HS(O)_{0-2}$—, ($C_1$-$C_6$ alkyl)$S(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_1$-$C_6$ alkyl)$S(O)_{0-2}$, ($C_1$-$C_6$ alkyl) C(O)NH—, HC(O)NH—, $H_2N$—C(NH)—, —$O(C_1$-$C_6$ alkyl)$CF_3$, ($C_1$-$C_6$ alkyl)C(O—, HC(O)—, ($C_1$-$C_6$ alkyl)OC (O)—, HOC(O)—, ($C_1$-$C_6$ alkyl)O($C_1$-$C_6$ alkyl)—, HO($C_1$-$C_6$ alkyl)-, ($C_1$-$C_6$ alkyl)C(O)$_{1-2}$($C_1$-$C_6$ alkyl)-, ($C_1$-$C_6$ alkyl) C(O)$_{1-2}$—, HC(O)$_{1-2}$($C_1$-$C_6$ alkyl)-, ($C_1$-$C_6$ alkyl)OC(O) NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

The term "heteroaryl", alone or in combination, means a 5 or 6-membered aromatic ring containing 1, 2, 3 or 4 heteroatoms independently selected from N, O or S, e.g., 5-membered rings containing one nitrogen (pyrrole), one oxygen (pyran) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (furan) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

Heteroaryl groups may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)$S(O)_{0-2}$—, $HS(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_1$-$C_6$ alkyl)$S(O)_{0-2}$—, ($C_1$-$C_6$ alkyl)C(O)NH—, HC(O)NH—, $H_2N$—C(NH)—, —$O(C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_{1l}$ $_{-C6}$ alkyl)O($C_1$-$C_6$ alkyl)-, HO($C_1$-$C_6$ alkyl)-, ($C_1$-$C_6$ alkyl)O—, ($C_1$-$C_6$ alkyl)C (O)$_{1-2}$($C_1$-$C_6$ alkyl)-, HC(O)$_{1-2}$($C_1$-$C_6$ alkyl)-, ($C_1$-$C_6$ alkyl) C(O)$_{1-2}$, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O)NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

The term "cycloalkyl", alone or in combination with other groups, unless indicated otherwise, means a saturated cyclic hydrocarbon ring system with 3 to 8 carbon atoms, e.g., cyclopropyl, cyclobutyl, cyclopentyl, cyclohexyl, cycloheptyl and cyclooctyl. This may be represented by "$C_{3-8}$ cycloalkyl" or "$C_3$-$C_8$ cycloalkyl"). When the intended meaning is other than this, for example, when the number of carbon atoms is in the range of three to six carbon atoms, this meaning is represented in like fashion as "$C_{3-6}$ cycloalkyl" or "$C_3$-$C_6$ cycloalkyl".

Cycloalkyl groups may be unsubstituted, or substituted with 1-3 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_1$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, H$_2$N—C(NH)—, —O($C_1$-$C_6$ alkyl)CF$_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, ($C_1$-$C_6$ alkyl)OC(O)NH—, HOC(O)N—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, where such substitution results in formation of a stable compound.

The compounds of the invention are useful for treating hypertension, Pulmonary Arterial Hypertension, congestive heart failure, angina, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of compounds of the invention for the preparation of a medicament for the treatment and/or prophylaxis of the above-mentioned diseases.

The above-mentioned compounds of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphorarnidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolirnidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891,SQ 34017, aliskiren ((2S,4S, 5S,7S)-N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600,SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide. Such combination can be achieved by combining two active ingredients in a single dosage formulation containing two independent active ingredients, e.g., an angiotensin II receptor antagonist and a nitrooxy cyclopentane derivative of the invention.

The dosage regimen utilizing the compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds of the invention, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, more preferably 25 mg/day to 150 mg/day, and more preferably 5 mg/day to 100 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg,. Advantageously, the compound of the invention may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The compounds of the invention can be administered in such oral forms as tablets, capsules and granules. The compounds of the invention are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis

Several methods for preparing the compounds of this invention are described in the following Schemes and Examples. Starting materials and intermediates are made from known procedures or as otherwise illustrated.

EXAMPLE 1

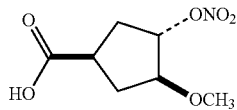

(+)-(1R,3S,4S)-3-methoxy-4-(nitrooxy)cyclopentanecarboxylic acid

Step A: methyl (1R,3s,5S)-6-oxabicyclo[3.1.0]hexane-3-carboxylate and methyl (1R,3r,5S)-6-oxabicyclo[3.1.0]hexane-3-carboxylate To a solution of methyl cyclopent-3-ene-1-carboxylate (5.05 g, 40.0 mmol) in dichloromethane (400 mL) at 0° C. was added 3-chloroperbenzoic acid (10.6 g, 46.0 mmol) portionwise. The reaction was stirred overnight at room temperature. The reaction was concentrated by half and then 300 mL of ether and 200 mL of aqueous potassium carbonate (sat) were added. The organic layer was washed with water, potassium carbonate, water then brine. The organic layer was dried over sodium sulfate and concentrated, and the residual clear oil was purified by chromatography on a 100-gram Biotage SNAP cartridge with 10 to 30% (6:3:1 hexane-cert-butyl methyl ether-acetonitrile)/hexane to give the trans epoxide, methyl (1R,3s,5S)-6-oxabicyclo[3.1.0]hexane-3-carboxylate. ¹H NMR (500 MHz, CDCl₃) δ 1.90 (dd, J=9.0, 14.0 Hz, 2H), 2.36 (dd, J=9.0, 14.0 Hz, 2H), 2.66 (quintet, J=9.0 Hz, 1H), 3.53 (s, 2H), 3.68 (s, 3H). Further elution of the column afforded the cis epoxide, methyl (1R,3r,5S)-6-oxabicyclo-[3.1.0]hexane-3-carboxylate. ¹H NMR (500 MHz, CDCl₃) δ 1.87 (dd, J=9.1, 14.1 Hz, 2H), 2.71 (d, J =14.1 Hz, 2H), 2.73 (t, J=9.0 Hz, 1H), 3.48 (s, 2H), 3.69 (s, 3H).

Step B: methyl (1RS,3RS,4RS)-3-hydroxy-4-methoxycyclopentanecarboxylate

To a solution of methyl (1R,3s,5S)-6-oxabicyclo[3.1.0] hexane-3-carboxylate (7.1 g, 50 mmol) in methanol (50 mL, 1236 mmol) was added concentrated sulfuric acid (0.023 mL, 0.431 mmol) and the solution was allowed to stir at room temperature. After 4 hours, silica gel TLC (40% Cert-butyl methyl ether/hexane) showed reaction was complete. The reaction was neutralized with a few drops of saturated aqueous sodium bicarbonate solution, and the methanol was removed under vacuum. The residue was dissolved in 200 mL dichloromethane, dried over sodium sulfate and filtered through a 2" thick pad of silica gel in a 600 mL fritted funnel. The pad was washed with 600 mL of dichloromethane (tlc showed no more product in eluate) and the combined filtrates were concentrated to give the racemic title compound as a clear oil. ¹H NMR (500 MHz, CDCl₃) δ 1.9 (m, 3H), 2.26 (m, 1H), 2.36 (m,1H), 3.03 (quintet, J=8.7 Hz, 1H), 3.37 (s, 3H), 3.62 (m, 1H), 3.71 (s, 3H), 4.24 (m, 1H).

Step C: (−)-methyl (1S,3R,4R)-3-methoxy-4-(nitrooxy)cyclopentanecarboxylate and (+)-methyl (1R,3S,4S)-3-methoxy-4-(nitrooxy)cyclopentanecarboxylate A sample of acetic anhydride (26.1 mL, 276 mmol) in a 1 L round bottom flask was cooled to 0° C. in an ice bath. To this was added fuming nitric acid (12.9 mL, 276 mmol), dropwise over a 10 minute period. The solution was stirred at 0° C. for 10 minutes more and then a solution of methyl (1RS,3RS,4RS)-3-hydroxy-4-methoxycyclopentanecarboxylate (18.5 g, 106 mmol) in 150 ml dichloromethane was added dropwise over a 15 minute period. This solution was stirred at 0° C. After 30 min, TLC (silica gel, 30% tent-butyl methyl ether-hexane) showed reaction was complete. The solution was diluted with 200 mL water and 500 mL dichloromethane, and the layers were separated. The aqueous layer was washed with 100 mL dichloromethane, and the combined organic layer was washed with three 200 mL portions of saturated sodium bicarbonate solution (watch out for pressure from carbon dioxide production), then when no more gas was produced, with 300 inL brine. The organic layer was dried over sodium sulfate and filtered through a 3" thick pad of silica gel in a 600 mL flitted funnel. The pad was washed with another 1 L of dichloromethane, and the combined filtrates were concentrated to give the racemic nitrate ester as a clear liquid. ¹H NMR (500 MHz, CDCl₃) δ 2.1 (m, 2H), 2.36 (m, 1H), 2.56 (m, 1H), 2.99 (quintet, J=8.7 Hz, 1H), 3.37 (s, 3H), 3.73 (s, 3H), 3.84 (m, 1H), 5.30 (m, 1H).

The racemic mixture was separated into its enantiomers by SFC on an OD column using 10% 3:1 hexane:isopropanol and 90% supercritical carbon dioxide. Faster enantiomer $[\alpha]_D$−14.5° (c=4.9, CHCl₃). Slower enantiomer $[\alpha]_D$+14.4° (c=5.0, CHCl₃).

Step D: (+)-(1R,3S,4S)-3-methoxy-4-(nitrooxy)cyclopentanecaxboxylic acid

A solution of (+)-methyl (1R,3S,4S)-3-methoxy-4-(nitrooxy)cyclopentanecarboxylate (0.66 g, 3.0 mmol) in methanol (12 mL) was cooled to 0° C. To this was added 4 N potassium hydroxide (1.50 mL, 6.00 mmol) dropwise over 10 minutes and the solution was stirred and allowed to warm to 10° C. over 3 hours. The reaction mixture was neutralized to pH 7 by addition of 0.5 mL concentrated hydrochloric acid and then the solution was concentrated under vacuum to remove methanol. To the residue was added 10 mL chloroform and 2 mL water and the pH was adjusted to 3-4 by addition of 2 M hydrochloric acid. The layers were separated and the aqueous layer was washed with two 15 mL portions of chloroform. The combined organic layers were washed with brine and dried over sodium sulfate to give the title compound as a colorless oil. $^1$H NMR (500 MHz, CDCl$_3$) δ 2.08-2.18 (m, 2H), 2.32-2.40 (m, 1H), 2.52-2.58 (m, 1H), 3.05 (quintet, J=8.3 Hz, 1H), 3.40 (s, 3H), 3.86 (m, 1H), 5.31 (m, 1H).

EXAMPLE 2

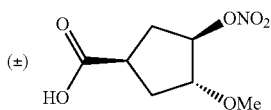

(1RS,3RS,4RS)-3-methoxy-4-(nitrooxy)cyclopentanecarboxylic acid

Step A: methyl (1RS,3RS,4RS)-3-methoxy-4-(nitrooxy)cyclopentanecarboxylate

The title compound was prepared by following steps A-C for example 1, except that the reagent methyl (1R,3s,5S)-6-oxabicyclo[3.1.0]hexane-3-carboxylate was replaced by methyl (1R,3r,5S)-6-oxabicyclo-[3.1.0]hexane-3-carboxylate in step B. $^1$H NMR (500 MHz, CDCl$_3$) δ 2.05-2.35 (m, 3H), 2.53-2.61 (m, 1H), 3.02-3.11 (m, 1H), 3.39 (s, 3H), 3.71 (s, 3H), 3.85-3.89 (m, 1H), 5.20-5.24 (m, 1H).

Step B: (1RS,3RS,4RS)-3-methoxy-4-(nitrooxy)cyclopentanecarboxylic acid

The title compound was prepared by following step D for example 1, except that the reagent (+)-methyl (1R,3S,4S)-3-methoxy-4-(nitrooxy)cyclopentanecarboxylate was replaced by methyl (1RS,3RS,4RS)-3-methoxy-4-(nitrooxy)cyclopentanecarboxylate. $^1$H NMR (500 MHz, CDCl$_3$) δ 2.10-2.19 (m, 3H), 2.57-2.65 (m, 1H), 3.14 (m, 1H), 3.41 (s, 3H), 3.90 (m, 1H), 5.23-5.27 (m, 1H).

EXAMPLE 3

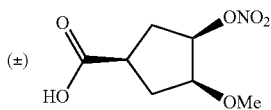

(1RS,3SR,4RS)-3-methoxy-4-(nitrooxy)cyclopentanecarboxylic acid

Step A: methyl (1s,3R,4S)-3,4-dihydroxycyclopentanecarboxylate and methyl (1r,3R,4S)-3,4-dihydroxycyclopentanecarboxylate To a stirred tent-butanol solution (500 mL) of methyl cyclopent-3-ene-1-carboxylate (26 g, 206 mmol) and 4-methylmorpholine N-oxide (26.6 g, 227 mmol) was added a 4% aqueous solution of osmium tetroxide (25.2 ml, 4.12 mmol) dropwise, and the mixture was stirred at room temperature. After 8 hours, the solution was concentrated to about 200 mL and then diluted with 300 mg sodium bisulfite and 250 mL water. The aqueous solution was extracted with three 300 mL portions of a 9:1 ether/dichloromethane mixture, and the combined organic layers were washed with aqueous sodium bicarbonate solution, water and brine. The organic extract was dried over sodium sulfate, filtered and concentrated. The oily residue was applied to column of silica gel in a 2 L fritted funnel that was packed in hexane. The column was eluted with step gradient of ether/hexane (500 mL portions of 10%, 20%, 30%, 40% and 50% ether/hexane), then with a step gradient of acetone/hexane (1 L portions of 5%, 10% and 15%). The column was then washed with 15% acetone/hexane to afford methyl (1s,3R,4S)-3,4-dihydroxycyclopentanecarboxylate. $^1$H NMR (500 MHz, CDCl$_3$) δ 1.90-2.06 (m, 2H), 2.08-2.16 (m, 2H), 2.58 (s br, 2H), 3.18 (m, 1H), 3.50 (s, 3H), 4.20 (m, 2H). Further elution of the column afforded methyl (1r,3R,4S)-3,4-dihydroxycyclopentanecarboxylate. $^1$H NMR (500 MHz, CDCl$_3$) δ 1.85-2.00 (m, 2H), 2.18-2.26 (m, 2H), 2.84 (m, 1H), 2.92 (s, br, 2H), 3.73 (s, 3H), 4.06 (m, 2H).

Step B: methyl (1RS,3SR,4RS)-3-hydroxy-4-methoxycyclopentanecarboxylate

Methyl (1r,3R,4S)-3,4-dihydroxycyclopentanecarboxylate (0.481 g, 3.00 mmol), freshly prepared silver oxide (0.348 g, 1.50 mmol) and methyl iodide (0.375 mL, 6.00 mmol) were combined in N,N-dimethylformamide and stirred for 3 hours. The reaction mixture was filtered through diatomaceous earth, which was washed with more ether (15 mL). The combined filtrate was washed with brine, dried over sodium sulfate and evaporated. Silica gel chromatography, eluting with 20-40% acetone/hexane, gave the title compound. $^1$H NMR (500 MHz, CDCl$_3$) δ 2.01-2.18 (m, 4H), 2.48 (s br, 1H), 2.77 (m, 1H), 3.40 (s, 3H), 3.60-3.65 (m, 1H), 3.71 (s, 3H), 4.10 (m, 1H).

Step C: methyl (1RS,3SR,4RS)-3-methoxy-4-(nitrooxy)cyclopentanecarboxylate

The title compound was prepared by following step C for example 1, except that the reagent methyl (1RS,3RS,4RS)-3-hydroxy-4-methoxycyclopentanecarboxylate was replaced by methyl (1RS,3SR,4RS)-3-hydroxy-4-methoxycyclopentanecarboxylate. NMR (500 MHz, CDCl$_3$) δ 2.14-2.40 (m, 4H), 2.82 (m, 1H), 3.37 (s, 3H), 3.73 (s, 3H), 3.86 (m, 1H), 5.29 (dd, J=6.0, 10.8 Hz, 1H).

Step D: (1RS,3SR,4RS)-3-methoxy-4-(nitrooxy)cyclopentanecarboxylic acid

The title compound was prepared by following step D for example 1, except that the reagent (+)-methyl (1R,3S,4S)-3-methoxy-4-(nitrooxy)cyclopentanecarboxylate was replaced by methyl (1RS,3SR,4RS)-3-methoxy-4-(nitrooxy)cyclopentanecarboxylate. $^1$H NMR (500 MHz, CDCl$_3$) δ 2.17-2.30

(m, 2H), 2.32-2.43 (m, 2H), 2.90 (m, 1H), 3.39 (s, 3H), 3.89 (m, 1H), 5.30 (dd, J=6.1, 10.6 Hz, 1H).

EXAMPLE 4

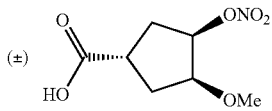

(±)

(1RS,3RS,4SR)-3-methoxy-4-(nitrooxy)cyclopentanecarboxylic acid

Step A: methyl (1RS,3RS,4SR)-3-methoxy-4-(nitrooxy)cyclopentanecarboxylate

The title compound was prepared by following steps A-C for example 3, except that the reagent methyl (1r,3R,4,9-3,4-dihydroxycyclopentanecarboxylate was replaced by methyl (1s,3R,4,9-3,4-dihydroxycyclopentanecarboxylate in step B. $^1$H NMR (500 MHz, CDCl$_3$) δ 2.13-2.28 (m, 3H), 2.34-2.41 (m, 1H), 3.08-3.12 (m, 1H), 3.40 (s, 3H), 3.71 (s, 3H), 4.00 (m, 1H), 5.41 (m, 1H).

Step B: (1RS,3RS,4SR)-3-methoxy-4-(nitrooxy)cyclopentanecarboxylic acid

The title compound was prepared by following step D for example 1, except that the reagent (+)-methyl (1R,3S,4S)-3-methoxy-4-(nitrooxy)cyclopentanecarboxylate was replaced by methyl (1RS,3RS,4SR)-3-methoxy-4-(nitrooxy)cyclopentanecarboxylate. $^1$H NMR (500 MHz, CDCl$_3$) δ 2.15-2.27 (m, 3H), 2.34-2.41 (m, 1H), 3.15-3.20 (m, 1H), 3.40 (s, 3H), 4.03 (m, 1H), 5.42 (m, 1H).

EXAMPLE 5

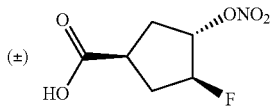

(±)

(1RS,3RS,4RS)-3-fluoro-4-(nitrooxy)eyciopentanecarboxylic acid

Step A: methyl (1RS,3RS,4RS)-3-fluoro-4-hydroxycyclopentanecarboxylate

To a dichloroethane solution (3 mL) of methyl (1R,3s,5S)-6-oxabicyclo[3.1.0]hexane-3-carboxylate (300 mg, 2.11 mmol) in a Teflon tube was added hydrogen fluoride-pyridine (0.190 mL, 2.11 mmol). The reaction mixture was stirred at room temperature for 6 hours, carefully poured onto 5 mL saturated aqueous sodium bicarbonate solution with ice, and extracted with three portions of dichloromethane. The combined organic extracts were dried over sodium sulfate, and chromatography over silica gel with 30-50% acetone/hexane gave the title compound. $^1$H NMR (500 MHz, CDCl$_3$) δ 1.96-2.03 (m, 1H), 2.12-2.32 (m, 3H), 2.38-2.52 (m, 1H), 3.12 (m, 1H), 3.72 (s, 3H), 4.34 (m, 1H), 4.86 (m, 1H).

Step B: methyl (1RS,3RS,4RS)-3-fluoro-4-(nitrooxy)cyclopentanecarboxylate

The title compound was prepared by following step C for example 1, except that the reagent methyl (1RS,3RS,4RS)-3-hydroxy-4-methoxycyclopentanecarboxylate was replaced by methyl (1RS,3RS,4RS)-3-fluoro-4-hydroxycyclopentanecarboxylate. $^1$H NMR (500 MHz, CDCl$_3$) δ 2.12-2.18 (m, 1H), 2.27-2.50 (m, 2H), 2.62 (m, 1H), 3.09 (m, 1H), 3.75 (s, 3H), 5.08 (m, 1H), 5.45 (m, 1H).

Step C: (1RS,3RS,4RS)-3-fluoro-4-(nitrooxy)cyclopentanecarboxylic acid

The title compound was prepared by following step D for example 1, except that the reagent (+)-methyl (1R,3S,4S)-3-methoxy-4-(nitrooxy)cyclopentanecarboxylate was replaced by methyl (1RS,3RS,4RS)-3-fluoro-4-(nitrooxy)cyclopentanecarboxylate. $^1$H NMR (500 MHz, CDCl$_3$) δ 2.13-2.52 (m, 1H), 2.30-2.52 (m, 2H), 2.61-2.69 (m, 1H), 3.16 (m, 1H), 5.10 (m, 1H), 5.47 (m, 1H).

EXAMPLE 6

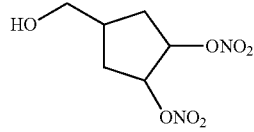

4-(hydroxymethyp)cyclopentane-1,2-diyl dinitrate

Step A: cyclopent-3-en-1-ylmethanol

A 2.0 M tetrahydrofuran solution of lithium aluminium hydride (11.2 mL, 22.5 mmol) was added dropwise to a tetrahydrofuran solution (45 mL) of 3-cyclopentene-1-carboxylic acid (2.33 mL, 22.5 mmol). The reaction mixture was stirred at room temperature for 16 hours. Water was added, and the solution was extracted with ethyl acetate. The combined organic layers were dried (magnesium sulfate), filtered, and concentrated in vacuo. The residue was purified by silica gel chromatography (Biotage 40M), eluting with 0-100% ethyl acetate/hexanes to give the title compound as a colorless oil. $^1$H NMR (500 MHz, CHCl$_3$) δ 2.04-2.11 (m, 2H), 2.20 (br s, 1H), 2.43-2.49 (m, 3H), 3.51 (d, J=5.3 Hz, 2H), 5.64 (s, 2H).

Step B: cyclopent-3-en-1-ylmethyl 4-nitrobenzoate

4-Nitrobenzoyl chloride (3.46 g, 18.7 mmol) was added to a dichloromethane solution (34 mL) of cyclopent-3-en-1-ylmethanol (1.67 g, 17.0 mmol) and triethylamine (3.55 mL, 25.4 mmol). The solution was stirred at room temperature for 15 minutes. Saturated aqueous sodium bicarbonate solution was added, and the solution was extracted with dichloromethane. The combined organic layers were dried (magnesium sulfate), filtered, and concentrated in vacuo. The residue was purified by silica gel chromatography (Biotage 40M), eluting with 0-100% ethyl acetate/hexanes to give the title compound as a white solid. $^1$H NMR (500 MHz, CHCl$_3$) δ 2.21 (dd, J=4.9, 14.8 Hz, 2H), 2.57 (dd, J=8.6, 15.1 Hz, 2H), 2.71-2.82 (m, 1H), 4.28 (d, J=7.2 Hz, 2H), 5.69 (s, 2H), 8.19 (d, J=8.6 Hz, 2H), 8.27 (d, J=8.6 Hz, 2H).

Step C: (3,4-dihydroxycyclopentyl)methyl 4-nitrobenzoate

Osmium tetroxide (235 μL, 0.75 mmol) was added to a solution of cyclopent-3-en-1-ylmethyl 4-nitrobenzoate (3.70 g, 15.0 mmol) and 4-methylmorpholine N-oxide (1.93 g, 16.5 mmol) in tent-butanol (6.7 mL)/water (40 mL)/acetone (13.3 mL). The solution was stirred at room temperature for 16 hours. Aqueous sodium bisulfite solution was added, and the solution was stirred for 30 min. The solution was then extracted with ethyl acetate, and the combined organic layers were dried (magnesium sulfate), filtered, and concentrated in vacua. The residue was purified by silica gel chromatography (Biotage 65i), eluting with 0-100% ethyl acetate/hexanes to give the title compound as a colorless oil. $^1$H NMR (500 MHz, CHCl$_3$) δ 1.67-1.75 (m, 2H), 1.95-2.00 (m, 2H), 2.80-2.85 (m, 1H), 4.21 (quintet, J=4.1 Hz, 2H), 4.26 (d, J=6.7 Hz, 2H), 8.19 (d, J=8.7 Hz, 2H), 8.29 (d, J=8.7 Hz, 2H).

Step D: [3,4-bis(nitrooxy)cyclopentyl]methyl 4-nitrobenzoate

Nitric acid (314 μL, 6.33 mmol) was added slowly to acetic anhydride (13 mL) at 0° C. (3,4-dihydroxycyclopentyl)methyl 4-nitrobenzoate (890 mg, 3.16 mmol) was then added, and the solution was stirred at 0° C. for 15 minutes. Saturated aqueous sodium bicarbonate solution was added, and the solution was extracted with ethyl acetate. The combined organic layers were dried (magnesium sulfate), filtered, and concentrated in vacuo. The residue was purified by silica gel chromatography (Biotage 40M), eluting with 0-100% ethyl acetate/hexanes to give the title compound as a white solid. $^1$H NMR (500 MHz, CHCl$_3$) δ 2.03-2.11 (m, 2H), 2.26-2.34 (m, 2H), 2.84-2.94 (m, 1H), 4.37 (d, J=6.3 Hz, 2H), 5.58-5.62 (m, 2H), 8.21 (d, J=8.7 Hz, 2H), 8.33 (d, J=8.5 Hz, 2H).

Step E: 4-(hydroxymethyl)cyclopentane-1,2-diyldinitrate

The title compound was prepared by following step D for example 1, except that the reagent (+)-methyl (1R,3S,4S)-3-methoxy-4-(nitrooxy)cyclopentanecarboxylate was replaced by [3,4-bis(nitrooxy)cyclopentyl]methyl 4-nitrobenzoate. $^1$H NMR (500 MHz, CHCl$_3$) δ 1.66 (s br, 1H), 1.99-2.07 (m, 2H), 2.12 (ddd, J=5.0, 9.4, 14.5 Hz, 2H), 2.48-2.58 (m, 1H), 3.61 (d, J=5.0 Hz, 2H), 5.50-5.55 (m, 2H).

EXAMPLE 7

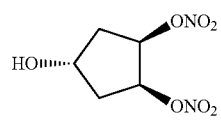

(1R,2S,4s)-4-Hydroxycyclopentane-1,2-diyl dinitrate

Step A: (1R,2S,4s)-4-(benzyloxy)cyclopentane-1,2-diol

Osmium tetroxide (300 mg) in t-butyl alcohol (90 mL) was added to a stirred mixture of 4-methylmorpholine N-oxide monohydrate (46.5 g, 0.34 mol) in water (420 mL) and acetone (270 mL). Benzyl cyclopent-3-en-1-yl ether (10 g, 38 mmol) was added to the mixture under nitrogen, and the resulting mixture was stirred overnight at room temperature. The reaction was treated with aqueous sodium hydrosulfite solution (200 mL), extracted with dichloromethane (3×100 mL), washed with brine (100 mL), dried over sodium sulfate, filtered and evaporated in vacuum. The residue was purified by column chromatography to give the title compound. $^1$H NMR (100 MHz, CHCl$_3$) δ 1.94-2.19 (m, 4H), 4.12-4.25 (m, 3H), 4.42 (s, 2H), 7.21-7.36 (m, 5H).

Step B: (3aR,5s,6aS)-5-(benzyloxy)-2,2-dimethyltetrahydro-3aH-cyclopenta[d][1,3]dioxole Toluenesulfonic acid monohydrate (270 mg, 1.4 mmol) was added to an acetone solution (100 mL) of (1R,2S,4s)-4-(benzyloxy)cyclopentane-1,2-diol (6.0 g, 29 mmol) and 2,2-dimethoxypropane (3.9 mL, 32 mmol). The mixture was stirred at room temperature for 3 hours. The solvent was removed in vacuum. The residue was diluted with sodium bicarbonate (50 mL) and extracted with diethyl ether (3×50 mL). The organic extracts were washed with sodium bicarbonate (50 mL), water (50 mL) and brine (50 mL), dried over magnesium sulfate and concentrated in vacuum. The residue was distilled to give the title compound. $^1$H NMR (400 MHz, CDCl$_3$) δ 1.27 (s, 3H), 1.41 (s, 3H), 1.57-1.85 (m, 2H), 2.19-2.26 (m, 2H), 4.18-4.26 (m, 1H), 4.49 (s, 2H), 4.65-4.67 (m, 2H), 7.24-7.36 (m, 5H).

Step C: (3aR,5s,6aS)-2,2-dimethyltetrahydro-3alf-cyclopenta[d][1,3]dioxol-5-yl 4-nitrobenzoate To a dichloromethane solution (150 mL) of the (3aR,5s,6aS)-5-(benzyloxy)-2,2-dimethyltetrahydro-3aH-cyclopenta[d][1,3]dioxole (8.0 g, 32 mmol), 2,3-dichloro-5,6-dicyano-p-benzoquinone (11 g, 48 mmol) was added. The resulting mixture was stirred for 3 hours at reflux. It was diluted with water (100 mL) and filtered, extracted with dichloromethane (3×200 mL), washed with brine, dried over sodium sulfate, filtered and concentrated in vacua to give a crude product. This crude product was dissolved in dichloromethane (100 mL), and triethylamine (10.6 mL, 76.0 mmol) was added. A dichloromethane solution (50 mL) of 4-nitrobenzoyle chloride (7.1 g, 38 mmol) was added dropwise at 0° C. The resulting mixture was stirred for 3 hours at room temperature and diluted with water (100 mL), extracted with dichloromethane (3×100 mL), washed with brine (50 mL), dried over sodium sulfate, filtered and concentrated in vacuo. The residue was purified by column chromatography to give the title compound. $^1$H NMR (400 MHz, CDCl$_3$) δ 1.29 (s, 3H), 1.47 (s, 3H), 1.77-1.84 (m, 2H), 2.43-2.48 (m, 2H), 4.73-4.75 (m, 2H), 5.50-5.55 (m, 1H), 8.17 (d, J=6.8 Hz, 2H), 8.26 (d, J=6.8 Hz, 2H).

Step D: (1s,3R,4S)-3,4-dihydroxycyclopentyl 4-nitrobenzoate

Hydrochloric acid (32.5 mL, 32.5 mmol, 1N in water) was added to a tetrahydrofuran solution (65 mL) of (3aR,5s,6aS)-2,2-dimethyltetrahydro-3aH-cyclopenta[d][1,3]dioxol-5-yl 4-nitrobenzoate (2.0 g, 6.51 mmol). The solution was stirred for 16 hours at room temperature. The solvent was removed in vacua. The residue was purified by silica gel chromatography (Biotage 65i), eluting with 0-20% methanol/dichloromethane to give the title compound as a white solid. $^1$H NMR (500 MHz, CHCl$_3$) δ 2.08-2.17 (m, 2H), 2.29-2.37 (m, 2H), 2.40 (s br, 2H), 4.31-4.39 (m, 2H), 5.52-5.59 (m, 1H), 8.16 (d, J=8.4 Hz, 2H), 8.27 (d, J=8.4 Hz, 2H).

Step E: (1s,3R,4S)-3,4-bis(nitrooxy)cyclopentyl 4-nitrobenzoate

The title compound was prepared by following step D for example 10, except that the reagent (3,4-dihydroxycyclopentyl)methyl 4-nitrobenzoate was replaced by (1s,3R,4S)-3,4-dihydroxycyclopentyl 4-nitrobenzoate. $^1$HNMR (500 MHz, CHCl$_3$) δ 2.47-2.53 (m, 2H), 2.55-2.63 (m, 2H), 5.54-5.65 (m, 1H), 5.72-5.76 (m, 2H), 8.20 (d, J=8.6 Hz, 2H), 8.30 (d, J=8.6 Hz, 2H).

Step F: (1R,2S,4s)-4-hydroxycyclopentane-1,2-diyl dinitrate

The title compound was prepared by following step D for example 1, except that the reagent (+)-methyl (1R,3S,4S)-3-methoxy-4-(nitrooxy)cyclopentanecarboxylate was replaced by (1s,3R,4S)-3,4-bis(nitrooxy)cyclopentyl 4-nitrobenzoate. $^1$H NMR (500 MHz, CHCl$_3$) δ 2.15-2.30 (m, 4H), 4.52-4.56 (m, 1H), 5.65-5.69 (m, 2H).

EXAMPLE 8

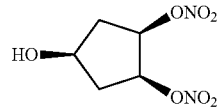

(1R, 2S, 4r)-4-Hydroxycyclopentane-1,2-diyl dinitrate

The title compound was prepared by following the procedure for example 11, except that the reagent (1R,2S,4s)-4-(benzyloxy)cyclopentane-1,2-diol was replaced by (1R,23,4r)-4-(benzyloxy)cyclopentane-1,2-diol (isolated as another diastereomer in step A, example 11) in step B. $^1$H NMR (500 MHz, CHCl$_3$) δ 2.03 (td, J=4.4, 15.1 Hz, 2H), 2.23 (s br, 1H), 2.40-2.65 (m, 2H), 4.36-4.42 (m, 1H), 5.42 (t, J=6.4 Hz, 2H).

EXAMPLE 9

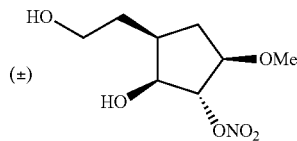

(1RS,2SR3SR,5RS)-2-hydroxy-3-(2-hydroxyethyl)-5-methoxycyclopentyl nitrate

Step A: cis-3,3a,4,6a-tetrahydro-2H-cyclopenta[b]furan-2-one

Tetrafluoroboric acid (2.50 mL, 15.9 mmol) was added to a solution of iodobenzene diacetate (5.10 g, 15.9 mmol) in acetic acid (13.2 mL). 2-Cyclopentene-1-acetic acid (955 μL, 7.93 mmol) was added and the solution was stirred at room temperature for 1 hour. The solution was then added to water and extracted with chloroform. The chloroform layer was extracted with water. The combined organic layers were dried (magnesium sulfate), filtered, and concentrated in vacuo. The residue was purified by silica gel chromatography (Biotage 40M), eluting with 0-100% ethyl acetate/hexanes to give the title compound as a colorless oil. $^1$H NMR (500 MHz, CHCl$_3$) δ 2.22-2.31 (m, 2H), 2.67-2.84 (m, 2H), 3.05-3.15 (m, 1H), 5.44-5.51 (m, 1H), 5.79-5.86 (m, 1H), 6.01-6.07 (m, 1H).

Step B: (1aRS,1bRS,4aSR,5aRS)-hexahydro-3H-oxireno[4,5]cyclopenta[1,2-b]furan-3-one 3-Chloroperbenzoic acid (1.3 g, 5.8 mmol) was added to a benzene solution (12 mL) of cis-3,3a,4,6a-tetrahydro-2H-cyclopenta[b]furan-2-one (600 mg, 4.83 mmol). The reaction mixture was stirred at room temperature for 3 hours. Saturated aqueous sodium bicarbonate solution was added, and the reaction mixture was extracted with dichloromethane. The combined organic layers were dried (magnesium sulfate), filtered, and concentrated in vacuo. The residue was purified by silica gel chromatography (Biotage 25M), eluting with 0-100% EtOAc/hexanes to give the title compound as a white solid. $^1$H NMR (500 MHz, CHCl$_3$) δ 1.55 (ddd, J=1.4, 7.2, 14.7 Hz, 1H), 2.34 (d, J=17.6 Hz, 1H), 2.49 (dd, J=8.6, 14.7 Hz, 1H), 2.68 (ddd, J=7.2, 8.8, 15.2 Hz, 1H), 2.76 (dd, J=9.0, 17.6 Hz, 1H), 3.62 (s, 1H), 3.74 (d, J=2.2 Hz, 1H), 4.90 (d, J=5.9 Hz, 1H).

Step C: (3aRS,5RS,6SR,6aSR)-6-hydroxy-5-methoxyhexahydro-2H-cyclopenta[b]furan-2-one Sulfuric acid (1.8 mL, 34 mmol) was added to a methanol solution (67 mL) of (1aRS,1bRS,4aSR,5aRS)-hexahydro-3H-oxireno[4,5]cyclopenta[1,2-b]furan-3-one (4.70 g, 33.5 mmol). The solution was stirred at room temperature for 2 hours. Saturated aqueous sodium bicarbonate solution was added, and the reaction mixture was extracted with ethyl acetate. The combined organic layers were dried (magnesium sulfate), filtered, and concentrated in vacuo. The residue was purified by silica gel chromatography (Biotage 40M), eluting with 0-100% ethyl acetate/hexanes to give the title compound as a colorless oil. $^1$H NMR (500 MHz, CHCl$_3$) δ 1.75 (td, J=3.5, 13.9 Hz, 1H), 2.27 (ddd, J=4.8, 8.8, 13.9 Hz, 1H), 2.39 (dd, J=3.6, 18.4 Hz, 1H), 2.76 (dd, J=11.2, 18.4 Hz, 1H), 2.95 (s, 1H), 3.00-3.09 (m, 1H), 3.32 (s, 3H), 3.63-3.71 (m, 1H), 4.30 (s, 1H), 4.74 (d, J=7.8 Hz, 1H).

Step D: (3aRS,5RS,6SR,6aSR)-5-methoxy-2-oxohexahydro-2H-cyclopenta[b]furan-6-yl nitrate The title compound was prepared by following step C for example 1, except that the reagent methyl (1RS,3RS,4RS)-3-hydroxy-4-methoxycyclopentanecarboxylate was replaced by (3aRS,5RS,6SR,6aSR)-6-hydroxy-5-rnethoxyhexahydro-2H-cyclopenta[b]furan-2-one. $^1$H NMR (500 MHz, CHCl$_3$) δ 1.89 (d, J=14.3 Hz, 1H), 2.18 (ddd, J=4.9, 8.6, 14.3 Hz, 1H), 2.42-2.48 (m, 1H), 2.75 (dd, J=11.1, 18.4 Hz, 1H), 3.06-3.13 (m, 1H), 3.35 (s, 3H), 3.83-3.88 (m, 1H), 4.85 (d, J=7.6 Hz, 1H), 5.31-5.35 (m, 1H).

Step E: (1RS,2SR,3SR,5RS)-2-hydroxy-3-(2-hydroxyethyl)-5-methoxycyclopentyl nitrate Borane dimethylsulfide complex (14.4 mL, 72.1 mmol) was added to a tetrahydrofuran solution (16 mL) of (3aRS, 5RS,6SR,6a5R)-5-methoxy-2-oxohexahydro-2H-cyclopenta[b]furan-6-yl nitrate (1.74 g, 8.01 mmol). The solution was stirred for 2 hours at room temperature. Methanol was added to quench the reaction. Water was added and the solution was extracted with ethyl acetate. The combined organic layers were dried (magnesium sulfate), filtered, and concentrated in vacua. The residue was purified by silica gel chromatography (Biotage 40M), eluting with 0-100% ethyl acetate/hexanes to give the title compound as a colorless oil. $^1$H NMR (500 MHz, CHCl$_3$) δ 1.64-1.77 (m, 2H), 1.83-1.93 (m, 1H), 2.02-2.13 (m, 1H), 2.20 (td, J =6.9, 12.6 Hz, 1H), 3.38 (s, 3H), 3.69 (dt, J=3.6, 9.5 Hz, 1H), 3.75-3.85 (m, 2H), 4.13 (d, J=5.1 Hz, 1H), 5.12 (d, J=3.5 Hz, 1H).

EXAMPLE 10

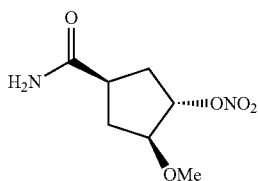

(1S,2S,4R)-4-carbamoyl-2-methoxycyclopentyl nitrate

To a dichloromethane solution (30 mL) of (1R,3S,4S)-3-methoxy-4-(nitrooxy)cyclopentanecarboxylic acid (example 1, 0.13 g, 0.64 mmol) was added triethylamine (0.72 mL, 5.1 mmol) and ethyl chlorofonnate (0.49 mL, 5.1 mmol) at 0° C. The reaction solution was stirred at 0° C. for 1 hour when aqueous ammonia (8.0 mL, 0.10 mol, 28% wt) was added. The reaction was stirred for another 16 hours at 0° C. The aqueous phase was extracted with dichloromethane (2×15 mL). The combined organics were washed with cold 5% sodium bicarbonate (30 mL) and dried over magnesium sulfate. The organics were concentrated in vacuo and purified by column chromatography, affording the title compound as a colorless liquid. $^1$H NMR (500 MHz, CDCl$_3$) δ 2.02 (ddd, J=3.7, 6.1, 14.5 Hz, 1H), 2.22 (dd, J=8.5, 15.3 Hz, 1H), 2.30-2.37 (m, 1H), 2.40-2.47 (m, 1H), 2.94 (quintet, J=6.2 Hz, 1H), 3.44 (s, 3H), 3.89-3.91 (m, 1H), 5.36 (d, J=6.1 Hz, 1H).

EXAMPLE 11

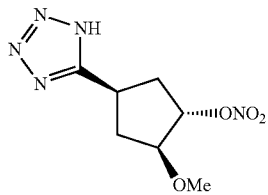

(1S,2S,4R)-2-methoxy-4-(1H-tetrazol-5-yl)cyclopentyl nitrate

To a N,N-dimethylformamide solution (6 mL) of (1S,2S,4R)-4-carbamoyl-2-methoxycyclopentyl nitrate (example 14, 0.091 g, 0.44 mmol) was added cyanuric chloride (75.0 mg, 0.41 mmol) at 0° C. The mixture was stirred for 4 hours, quenched with water (20 mL) and partitioned with ethyl acetate (3×25 mL). The combined organics were washed with water, brine, dried over magnesium sulfate, and concentrated in vacuo. The residue was added to a solution of glacial acetic acid (0.10 mL, 1.8 mmol) and triethylamine (0.25 mL, 1.8 mmol) in toluene (2 mL). Sodium azide (0.12 g, 1.8 mmol) was added to the solution and heated to reflux for 24 hours. The mixture was allowed to cool to room temperature before quenching with water. The mixture was partitioned with water (4 mL). The organic layer was then treated with IN hydrochloric acid (5 mL) and partitioned with ethyl acetate (3×10 mL). The combined organics were washed with brine, dried over magnesium sulfate, and concentrated in vacuo. The residue was crystallized from ethyl acetate and hexanes to afford the title compound as a yellow crystalline solid. $^1$H NMR (500 MHz, CH$_3$CN) δ 1.93-1.95 (m, 1H), 2.36-2.42 (m, 1H), 2.45-2.53 (m, 1H), 2.55-2.64 (m, 1H), 3.37 (s, 3H), 3.66 (quintet, J=8.7 Hz, 1H), 3.89-3.91 (m, 1H), 5.4 (d, J=6.4 Hz, 1H).

EXAMPLE 12

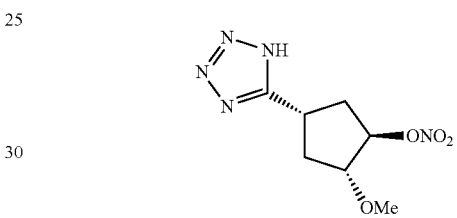

(1R,2R,4S)-2-methoxy-4-(1H-tetrazol-5-yl)cycl op entyl nitrate

The title compound was prepared by following the procedure for example 15, except that the reagent (1S,2S,4R)-4-carbamoyl-2-methoxycyclopentyl nitrate was replaced with (1R,2R,4S)-4-carbamoyl-2-methoxycyclopentyl nitrate.

EXAMPLE 13

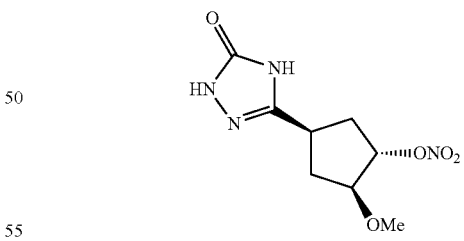

(1S,2S,4R)-2-methoxy-4-(5-oxo-4,5-dihydro-1H-1,2,4-triazol-3-yl)cyclopentyl nitrate (1S,2S,4R)-4-carbamoyl-2-methoxycyclopentyl nitrate (example 14, 0.14 g, 0.68 mmol) and bis(2-oxo-3-oxazolidinyl)phosphinic chloride (0.19 g, 0.75 mmol) were stirred for 10 minutes in dichloromethane (5 mL) and triethylamine (0.29 mL, 2.1 mmol). Semicarbazide hydrochloride (0.082 g, 0.73 mmol) was added and stirred at room temperature for 4 days. The solution was concentrated in vacuo and brought up in 1 M sodium hydroxide (3 mL, 3.0 mmol) to reflux for 8 hours. Purification of the crude product by reversed-phase mass-directed high-performance liquid chromatography afforded the title compound as a colorless liquid. $^1$H NMR (500 MHz, CDCl$_3$) δ 1.93-1.98 (m, 1H), 2.34 (dd, J=4.1, 8.3 Hz, 2H), 2.40-2.47 (m, 1H), 2.40-2.47 (m, 1H), 3.42 (quintet, J=6.2 Hz, 1H), 3.50 (s, 3H), 3.93-3.96 (m, 1H), 5.40-5.43 (m, 1H).

EXAMPLE 14

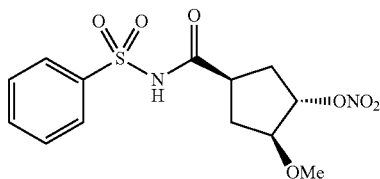

(1S,2S,4R)-2-methoxy-4-[(phenylsulfonyl)carbamoyl]cyclopentyl nitrate

A mixture of (1R,3S,4S)-3-methoxy-4-(nitrooxy)cyclopentanecarboxylic acid (example 1, 105 mg, 0.510 mmol) and benzenesulfonamide (173 mg, 1.10 mmol) was dissolved in dichloromethane (4 mL). Triethylamine (240 pl, 1.72 mmol) was added, followed by O-(7-azabenzotriazol-1-yl)-N,N,N',N'-tetramethyluronium hexafluorophosphate (291 mg, 0.765 mmol). The reaction mixture was stirred for 12 hours. Purification of the crude product by reversed-phase mass-directed high-performance liquid chromatography afforded the title compound as a white solid. $^1$H NMR (500 MHz, CDCl$_3$) δ 1.93-2.02 (m, 1H), 2.15-2.26 (m, 2 H), 2.34 (dt, J=6.8, 15.7 Hz, 1H), 2.93-3.01 (m, 1H), 3.50 (s, 3H), 3.90-3.94 (m, 1H), 5.33-5.37 (m, 1H), 7.55 (t, J=7.8 Hz, 2H), 7.65 (t,J=7.5 Hz, 1H), 8.03-8.07 (m, 2H), 9.42 (s, 1H).

EXAMPLE 15

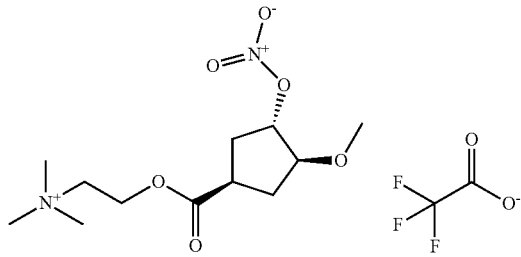

4-[(1S,3S,4S)-3-methoxy-4-nitrocyclopentyl]-N,N,N-trimethyl-4-oxobutan-1-aminium trifluoroacetate To a solution of (1R,3S,4S)-3-methoxy-4-(nitrooxy)cyclopentanecarboxylic acid (1 g, 5.31 mmol) in 10 mL acetonitrile at rt was added choline hydrochloride (1.11 g, 7.97 mmol) and followed by PyBOP (4.15 g, 7.97 mmol), Et$_3$N (1.85 mL, 1.34 mmol). After stirring at rt over night, the mixture was purified by Waters Mass-Directed Purification Systems (Waters 30×100 mm, 5 μm, SunFire C18, flow rate 50 mL/min, gradient over 15 min: 10-100% AcCN/H$_2$O with 0.1% TFA), affording the title compound: $^1$H NMR (500 MHz, CDCl$_3$) δ 5.29 (m, 1H), 4.45(m, 2H), 3.91 (m, 1H), 3.64 (m, 2H), 3.28 (s, 3H), 3.11 (s, 9H), 3.03 (m, 1H), 2.49 (m, 1H), 2.39 (m, 1H), 2.09 (m, 1H), 1.87 (m, 1H).

EXAMPLE 16

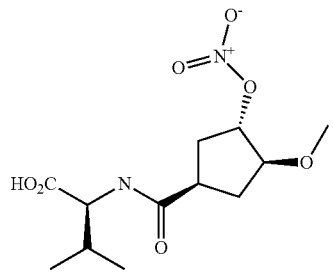 [SMILES: CO[C@H]1C[C@@H](C(=O)N[C@H](C(=O)O)C(C)C)C[C@@H]1O[N+](=O)[O-]]

N-{[(1R,3S,4S)-3-methoxy-4-(nitrooxy)cyclopentyl]carbonyl}-L-valine

Step A: methyl N-{[1R,3S,4S)-3-methoxy-4-(nitrooxy)cyclopentyl]carbonyl}-L-valinate To a solution of L-valine methyl ester hydrochloride (633 mg, 3.78 mmol), (1R,3S,4S)-3-methoxy-4-(nitrooxy)cyclopentanecarboxylic acid (755 mg, 3.78 mmol), and triethylamine (1.05 mL, 7.55 mmol) in dichloromethane (30 mL) was added PyBOP (2.95 g, 5.67 mmol). After stirring at rt overnight, the mixture was washed saturated NaHCO$_3$ (3×50 mL) and brine (50 mL), dried over MgSO$_4$, and concentrated. The residue was purified by flash chromatography (RediSepRf 80 g) using 0-40% EtOAc/hexane gradient, affording the title compound (1.04 g, yield 86%): $^1$H NMR (500 MHz, CDCl$_3$) δ 6.50 (d, J=8.6, 1H), 5.40 (d, J=6.0, 1H), 4.55 (dd, J=4.7, 8.8, 1H), 3.92 (m, 1H), 3.77 (s, 3H), 3.47 (s, 3H), 2.96-2.91 (m, 1H), 2.52-2.46 (m, 1H), 2.38-2.32 (m, 1H), 2.24-2.17 (m, 2H), 2.07-2.01 (m, 1H), 0.97 (d, J=6.9, 3H), 0.92 (d, J=6.9, 3H).

Step B: N-{[(1R,3S,4S)-3-methoxy-4-(nitrooxy) cyclopentyl]carbonyl}-L-valine

To a solution of methyl N-{[(1R,3S,4S)-3-methoxy-4-(nitrooxy)cyclopentyl]carbonyl}-L-valinate (1.04 g, 3.27 mmol) in EtOH (10 mL) was added NaOH (5.0 N, 1.0 mL). After stirring at rt overnight, the mixture was partitioned between Et$_2$O/H$_2$O. The aq layer was extracted and acidified using 5.0 N HCl until pH-3 and then extracted with Et$_2$O (50 mL). The organic layer was washed with brine (2×50 mL), dried over Na$_2$SO$_4$, and concentrated to give the title compound as a white solid (810 mg, yield 81%): $^1$H NMR (500 MHz, CDCl$_3$) δ 6.70 (d, J=8.4, 1H), 5.40 (d, J=6.0, 1H), 4.53 (dd, J=4.6, 8.5, 1H), 3.93 (m, 1H), 3.48 (s, 3H), 3.03-2.96 (m, 1H), 2.53-2.46 (m, 1H), 2.38-2.20 (m, 3H), 2.08-2.02 (m, 1H), 1.01 (d, J=6.9, 3H), 0.97 (d, J=6.9, 3H).

Intermediate X

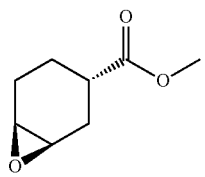

(1R,3S,6S)-methyl 7-oxabicyclo[4.1.0]heptane-3-carboxylate

Step A: (S)-cyclohex-3-enecarboxylic acid

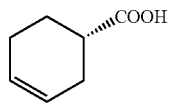

(S)-cyclohex-3-enecarboxylic acid (R)-(−)-α-methyl benzylamine salt was obtained after 6 re-crystallizations steps from acetone as described by Harold M. Schwartz et al. in J. Am. Chem. Soc., 1978, 100(16), pp 5199-5203). The chiral salt was re-dissolved in a aqueous solution at pH3 and the chiral acid was extracted twice with $CH_2Cl_2$; the organic layer was dried over $Na_2SO_4$, concentrated and used without any purification in the next reaction.

E. e.: 96%©.

$^1$H NMR (300 MHz, CDCl$_3$) δ 1.66-1.83 (m, 1H), 2.01-2.23 (m, 3H), 2.27-2.39 (m, 2H), 2.57-2.70 (m, 1H), 5.71 (m, 2H).

Step B (1R,3S,6S)-methyl 7-oxabicyclo[4.1.0]heptane-3-carboxylate

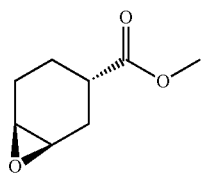

To a solution of (S)-cyclohex-3-enecarboxylic acid (2.7 g, 21.4 mmol) in methanol (20 ml), concentrated sulfuric acid (0.160 ml, 3.01 mmol) at room temperature was added; the mixture was stirred at reflux for 4 hours. Then the mixture was concentrated, diluted with $CH_2Cl_2$ and washed with a saturated solution of $NaHCO_3$ (2×50 mL) and brine (40 mL). The organic layer was dried over $Na_2SO_4$ and concentrated to a volume of about 4 mL. The residue was diluted in dichloromethane (210 mL) and, at 0° C., 3-chloroperbenzoic acid (6.28 g, 36.4 mmol) was added portionwise. The reaction was stirred overnight at rt. Then to the mixture, at 0° C., $Na_2S_2O_3$ (6.0 g) was added and stirred for 10 min. The mixture was diluted with dichloromethane and washed twice with a saturated solution of $NaHCO_3$ (2×50 mL); the organic layer was dried over $Na_2SO_4$ and concentrated in vacua. The residual oil was purified by chromatography on a 100G Biotage Snap cartridge with 5% to 40% EtOAc in Hex to give 1.32 g of trans epoxide, (1R,3S,6S)-methyl 7-oxabicyclo[4.1.0]heptane-3-carboxylate, Intermediate X.

$^1$H NMR (300 MHz, CDCl$_3$) δ 1.36-1.51 (m, 1H), 1.72-1.84 (m, 1H), 1.86-2.07 (m, 3H), 2.23-2.35 (m, 1H), 2.47-2.60 (m, 1H), 3.16 (m. 1H), 3.25 (m, 1H), 3.69 (s, 3H).

Intermediate Y (1S,3S,6R)-methyl 7-oxabicyclo[4.1.0]heptane-3-carboxylate

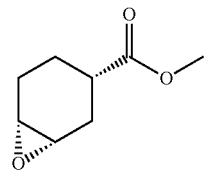

Further elution of the column described in Step B Intermediate X afforded 0.810 g of the cis epoxide, (1S,3S,6R)-methyl 7-oxabicyclo[4.1.0]heptane-3-carboxylate, Intermediate Y.

$^1$H NMR (300 MHz, CDCl$_3$) δ 1.55-1.70 (m, 2H), 1.72-1.85 (m, 1H), 2.12-2.32 (m, 4H), 3.18 (m, 2H), 3.69 (s, 3H).

Intermediates Z and W

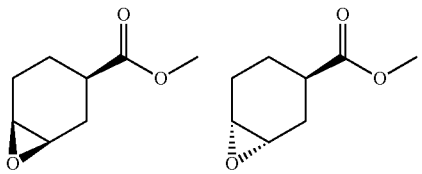

Intermediate Z: (1R,3R,6S)-methyl 7-oxabicyclo[4.1.0]heptane-3-carboxylate

Intermediate W (1S,3R,6R)-methyl 7-oxabicyclo[4.1.0]heptane-3-carboxylate

The two epoxides were prepared in two steps from (R)-cyclohex-3-enecarboxylic acid (Harold M. Schwartz et al. in J. Am. Chem. Soc., 1978, 100(16), pp 5199-5203)

| INTERMEDIATE | Name | $^1$H NMR (300 MHz, CDCl$_3$) |
|---|---|---|
| INTERMEDIATE Z 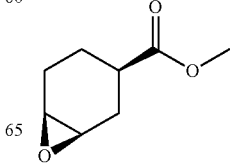 | (1R,3R,6S)-methyl 7-oxabicyclo[4.1.0] heptane-3-carboxylate | δ 1.55-1.70 (m, 2H), 1.72-1.85 (m, 1H), 2.12-2.32 (m, 4H), 3.18 (m, 2H), 3.69 (s, 3H). |

29
-continued

| INTERMEDIATE | Name | $^1$H NMR (300 MHz, CDCl$_3$) |
|---|---|---|
| INTERMEDIATE W | (1S,3R,6R)-methyl 7-oxabicyclo[4.1.0]heptane-3-carboxylate | δ 1.36-1.51 (m, 1H), 1.72-1.84 (m, 1H), 1.86-2.07 (m, 3H), 2.23-2.35 (m, 1H), 2.47-2.60 (m, 1H), 3.16 (m, 1H), 3.25 (m, 1H), 3.69 (s, 3H). |

EXAMPLE 17

(1S,3R,4R)-methyl 4-methoxy-3-(nitrooxy)cyclohexanecarboxylate

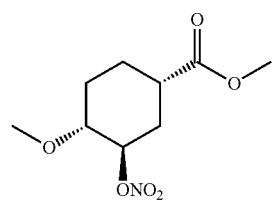

Step A: (1S,3R,4R)-methyl 3-hydroxy-4-methoxycyclohexanecarboxylate

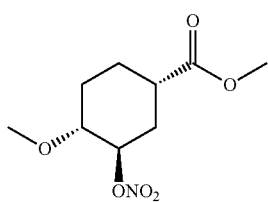

To a solution of Intermediate X (1.32 g, 8.48 mmol) in methanol (13 ml) concentrated sulfuric acid (0.005 ml, 0.0848 mmol) was added and the solution was allowed to stir at rt for 4h. The reaction was neutralized with a few drops of saturated aqueous NaHCO$_3$ and the methanol was removed under vacuum. The residue was dissolved in 40 ml of dichloromethane and washed with brine (20 ml). The organic layer was dried over sodium sulfate, filtered and evaporated in vacuo. The residue was purified by chromatography on a 100G Biotage Snap cartridge with 12% to 100% EtOAc in Hex, to give 1.36 g of (1S,3R,4R)-methyl 3-hydroxy-4-methoxycyclohexanecarboxylate as a clear oil $^1$H NMR (300 MHz, CDCl$_3$) δ 1.36-1.65 (m, 3H), 1.91-2.01 (m, 1H), 2.01-2.15 (m, 1H), 2.25-2.37 (m, 1H), 2.70-2.80 (m, 1H), 3.00-3.09 (m, 1H), 3.38 (s, 3H), 3.65-3.78 (m, 4H).

Step B: (1S,3R,4R)-methyl 4-methoxy-3-(nitrooxy)cyclohexanecarboxylate

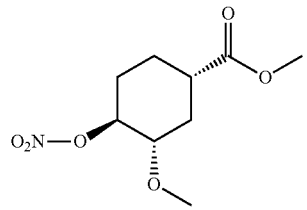 [SMILES: COC(=O)[C@H]1CC[C@H](O[N+](=O)[O-])[C@@H](OC)C1]

To a solution of acetic anhydride (1.36 ml, 14.5 mmol) in 12 ml of dichloromethane fuming nitric acid (0.659 ml, 15.9 mmol), was added at -20° C. After 15 min (1S,3R,4R)-methyl 3-hydroxy-4-methoxycyclohexanecarboxylate dissolved in 11 ml of dichloromethane was added. The solution was stirred at 0° C. for 3 hours. The mixture was poured in a becker with ice and NaHCO$_3$ as solid, then the product was extracted twice with dichloromethane. The organic layer was dried over sodium sulfate, filtered and evaporated in vacuo. The residue was purified by chromatography on a 50G Biotage Snap cartridge with 2% to 20% EtOAc in Hex, in 10 volumes of eluent to give 1.51 g of the title compound as a yellow oil.

$^1$H NMR. (300 MHz, CDCl$_3$) δ 1.66-2.02 (m, 5H), 2.16-2.29 (m, 1H), 2.59-2.73 (m, 1H), 3.37-3.46 (m, 4H), 3.71(s, 3H).

EXAMPLE 18

(1S,3S,4S)-methyl 3-methoxy-4-(nitrooxy)cyclohexanecarboxylate

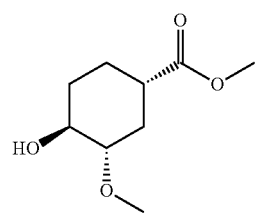

Step A: (1S,3S,4S)-methyl 4-hydroxy-3-methoxycyclohexanecarboxylate

Further elution of the column described in Example 17Step A afforded 0.060 g of (1S,3S,4S)-methyl 4-hydroxy-3-methoxycyclohexanecarboxylate.

$^1$H NMR (300 MHz, CDCl$_3$) δ 1.24-1.58 (m, 3H), 1.95-2.14 (m, 2H), 2.31-2.45 (m, 2H), 2.96-3.06 (m, 1H), 3.39-3.51 (m, 4H), 3.70 (s, 3H).

Step B: (1S,3R,4R)-methyl 3-methoxy-4-(nitrooxy)cyclohexanecarboxylate

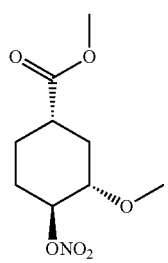

The title compound was prepared from compound obtained in Step A by following the procedure described in Example 17, Step B, $^1$H NMR (300 MHz, CDCl$_3$) δ 1.39-1.72 (m, 4H), 2,01-2.13 (m, 1H), 2.18-2.30 (m, 1H), 2.32-2.51 (m, 2H), 3.20-3.31 (m, 1H), 3.42 (m, 3H), 3.72 (m, 3H), 4.90-5.01 (m, 1H).

EXAMPLE 19

(1S,3R,4R)-methyl 3-methoxy-4-(nitrooxy)cyclohexanecarboxylate

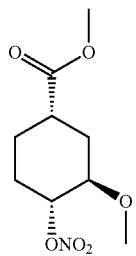

Step A: (1S,3R,4R)-methyl 4-hydroxy-3-methoxycyclohexanecarboxylate

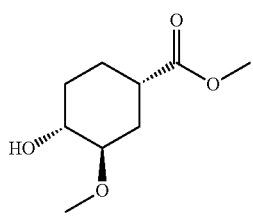

Starting from Intermediate Y and following procedure analogue to that described in Example 17

Step A the title compounds as a clear oil.

$^1$H NMR (300 MHz, CDCl$_3$) δ 1.41-1.67 (m, 3H), 1.85-1.97 (m, 1H), 2.02-2.14 (m, 2h), 2.32-2.43 (m, 1H), 2.71-2.80 (m, 1H), 3.19-3.29 (m, 1H), 3.41 (s, 3H), 3.51-3.62 (m, 1H), 3.71 (m, 3H).

Step B: (1S,3R,4R)-methyl 3-methoxy-4-(nitrooxy)cyclohexanecarboxylate

The title compound was prepared from (1S,3R,4R)-methyl 4-hydroxy-3-methoxycyclohexanecarboxylate by following the procedure analogous to that described for Example 17Step B.

$^1$H NMR (300 MHz, CDCl$_3$) δ 1.73-2.06 (m, 6H), 2.65-2.78 (m, 1H), 3.43 (s, 3H), 3.52-3.60 (m, 1H), 3.69 (s, 3H), 5.02-5.10 (m, 1H).

EXAMPLE 20

(1S,3S,4S)-methyl 4-methoxy-3-(nitrooxy)cyclohexanecarboxylate

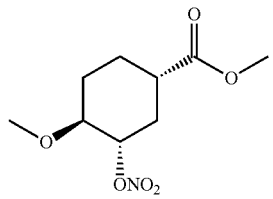

Step A: (1S,3S,4S)-methyl 3-hydroxy-4-methoxycyclohexanecarboxylate

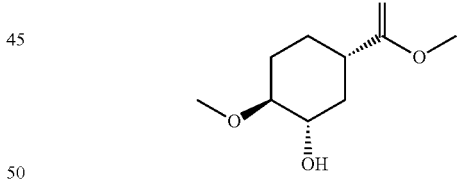

Form the purification of the reaction described in Example 19Step A also the title compound was obtained $^1$H NMR (300 MHz, CDCl$_3$) δ 1.08-1.26 (m, 1H), 1.36-1.60 (m, 2H), 1.96-2.09 (m, 1H), 2.14-2.32 (m, 2H), 2.35-2.49 (m, 1H). 2.92-3.04 (m, 1H), 3.37-3.54 (m, 4H), 3.69 (m, 3H).

Step B: (1S,3S,4S)-methyl 4-methoxy-3-(nitrooxy)cyclohexanecarboxylate

The title compound was obtained by nitrating compound obtained in Step A as described for analogous compounds.

$^1$H NMR (300 MHz, CDCl$_3$) δ 1.29-1.77 (m, 3H), 2.01-2.12 (m, 1H), 2.20-2.31 (m, 1H), 2.35-2.58 (m, 2H), 3.15-3.27 (m, 1H), 3.42 (s, 3H), 3.70 (s, 3H), 4.90-5.02 (m, 1H).

EXAMPLES 21-24

Following the procedures described for Example 17-20, but starting from intermediate W and Z the following compounds were obtained

| EXAMPLE | Name | $^1$H NMR (300 MHz, CDCl$_3$) |
|---|---|---|
| EXAMPLE 21 | (1R,3S,4S)-methyl 4-methoxy-3-(nitrooxy)cyclohexanecarboxylate | δ 1.36-1.65 (m, 3H), 1.91-2.01 (m, 1H), 2.01-2.15 (m, 1H), 2.25-2.37 (m, 1H), 2.70-2.80 (m, 1H), 3.00-3.09 (m, 1H), 3.38 (s, 3H), 3.65-3.78 (m, 4H). |
| EXAMPLE 22 | (1R,3R,4R)-methyl 3-methoxy-4-(nitrooxy)cyclohexanecarboxylate | δ 1.39-1.72 (m, 4H), 2.01-2.13 (m, 1H), 2.18-2.30 (m, 1H), 2.32-2.51 (m, 2H), 3.20-3.31 (m, 1H), 3.42 (m, 3H), 3.72 (m, 3H), 4.90-5.01 (m, 1H). |
| EXAMPLE 23 | (1R,3S,4S)-methyl 3-methoxy-4-(nitrooxy)cyclohexanecarboxylate | δ 1.41-1.67 (m, 3H), 1.85-1.97 (m, 1H), 2.02-2.14 (m, 2H), 2.32-2.43 (m, 1H), 2.71-2.80 (m, 1H), 3.19-3.29 (m, 1H), 3.41 (s, 3H), 3.51-3.62 (m, 1H), 3.71 (m, 3H). |
| EXAMPLE 24 | (1R,3R,4R)-methyl 4-methoxy-3-(nitrooxy)cyclohexanecarboxylate | δ 1.29-1.77 (m, 3H), 2.01-2.12 (m, 1H), 2.20-2.31 (m, 1H), 2.35-2.58 (m, 2H), 3.15-3.27 (m, 1H), 3.42 (s, 3H), 3.70 (s, 3H), 4.90-5.02 (m, 1H). |

Mononitrate compounds that have been orally dosed to rats result in nitrites (metabolites of nitric oxide) circulating in plasma with maximal concentrations in the 0.5-2 μM range. Similar dosing of mononitrate compounds described in this invention results in increased circulating nitrite concentrations. Biochemical evidence for the generation of NO in vivo in response to test compound administration was obtained from studies in Sprague-Dawley rats. Administration of test compound to fasted SD rats (40 mpk, PO) results in the appearance of reactive nitrogen species (RNS), assessed using the diaminonapthalene derivitization (DAN) assay.

RNS were detected as S-nitrosothiols (RNSOs) in EDTA-treated rat plasma using an HPLC fluorescent assay based on the method of Kostka and Park (Methods Enzymol. 1999, 301, 227-235). The method is based on the detection of fluorescent 2,3-naphthotriazole (NAT) formed in the reaction between acidified 2,3-diaminonaphthalene and the nitrosonium moiety of RSNOs released by $HgCl_2$-mediated breakdown of the S—NO bond. The reaction mixture was chromatographed by reversed phase HPLC, and the fluorescent signal of the resolved NAT peak was quantified.

Plasma (20 μL) was first diluted 1:1 in $H_2O$ (20 μL) in a black polypropylene untreated microtiter plate. DAN reagent (100 μL per well, 100 μM DAN in 0.1 N HCl, 4 mM $HgCl_2$) was added, and the plate was immediately sealed with an opaque plate mat, vortexed, and incubated in the dark for 10 mM. Plates were centrifuged (2000×g, 5 min) and chilled to 4° C. before HPLC analysis. HPLC was carried out on an Agilent 1200 system using a chilled autosampler (4° C.). Samples were chromatographed on a C8 column (Zorbax Eclipse XDB-C8, 4.6×150 mm, 5 μm) with isocratic elution using a mobile phase of 67% MeOH, 0.1% $NH_4OAc$ and a flow rate of 2 mL/min. NAT fluorescence was monitored at 450 nm using an excitation wavelength of 360 nm. Calibration curves were prepared using $NaNO_2$ in control plasma.

Vessel Relaxation

The ability of the compounds of the invention to induce vasorelaxation was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, $NaHCO_3$ 14.9, $KH_2PO_4$ 1.2, $MgSO_4$ 1.2, HEPES 10, $CaCl_2$, ascorbic acid 170 and glucose 1.1 (95% $O_2$/5% $CO_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 μM) and, when the contraction was stable, acetylcholine (ACh, 10 μM) was added. A relaxant response to ACh indicated the presence of a functional endothelium. Vessels that were unable to contract NA or showed no relaxation to ACh were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 μM) for 20 min.

Responses to relaxing agents are expressed as a percentage of residual contraction and plotted against concentration of test compound. $EC_{50}$ values (where $EC_{50}$ is the concentration producing 50% of the maximum relaxation to the test compound) were interpolated from these plots.

During the experimental period, the plateau obtained with NA was stable without significant spontaneous loss of contraction in the aortic rings.

As shown in data Table 1, the compounds of the invention were able to induce relaxation in a concentration-dependent manner. Furthermore, in experiments performed in the presence of ODQ (10 μM), the vasorelaxant responses to tested compounds were inhibited.

TABLE 1

Vessel Relaxation Data

| Compound | $EC_{50}$ (μM) | Max. Relaxation (%) |
|---|---|---|
| Vehicle | >1000 | 6.3 @ 1 μM |
| Example 1 | 126 | 37.47 @ 1 μM |
| Example 7 | 4.7 | 78 @ 30 μM |
| Example 8 | 4.4 | 69 @ 30 μM |
| Example 21 | 1.0 ± 0.2 | |
| Example 23 | 3.5 ± 0.6 | |
| Example 24 | 11.1 ± 4.5 | |
| Example 22 | 6.3 ± 2 | |
| SNAP (S-nitroso-N-acetylpenicillamine) | 0.237 | 97.3 |

What is claimed is:

1. A compound having the general formula I:

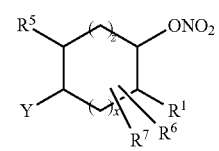

or a pharmaceutically acceptable salt thereof, wherein
X is 1;
Z is 1;
Y is selected from the group consisting of —C(O)OR², —(CH₂)₁₋₂OR³, —OH,

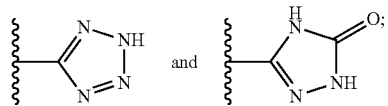 [SMILES: *c1nn[nH]n1 ; *c1n[nH]c(=O)[nH]1]

$R^1$ is selected from the group consisting of
1) —ONO₂,
2) —O—CH₃,
3) —O—aryl,
4) —O—heteroaryl,
5) —O—$C_{3-8}$ cycloalkyl,
6) -aryl,
7) -heteroaryl,
8) —$C_{3-8}$ cycloalkyl, and
9) halogen;
$R^2$ is selected from the group consisting of
1) hydrogen
2) —$C_{1-6}$ alkyl,
3) -aryl,
4) —CH₂OC(O)$C_{1-6}$ alkyl, and
5) —(CH₂)₁₋₂N⁺(R⁹)₃;

$R^3$ is selected from the group consisting of
1) hydrogen,
2) —C(O)$C_{1-6}$ alkyl, and
3) —P(O)(OH)$_2$, $R^5$ is selected from the group consisting of hydrogen and —OH;

$R^6$ is selected from the group consisting of hydrogen and —OH;

$R^7$ is absent or, when x is 2 or 3, is selected from the group consisting of hydrogen and —OH;

$R^8$ is selected from the group consisting of hydrogen, —CH($R^{10}$)COOH,

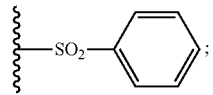

$R^9$ in each instance in which it occurs, is independently $C_{1-3}$ alkyl; and $R^{10}$ is straight or branched $C_{1-6}$ alkyl, wherein alkyl is unsubstituted or substituted on any carbon atom with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$cycloalkyl, $C_2$-$C_6$ alkenyl, $C_2$-$C_6$ alkynyl, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, wherein aryl is unsubstituted or substituted on any carbon atom with halogen, $C_1$-$C_{20}$ alkyl, $CF_3$, $NH_2$, —NH($_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C^{10}$ cycloalkyl, $C_2$-$C_6$ alkenyl, $C_2$-$C_6$ alkynyl, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, wherein cycloalkyl unsubstituted or substituted on any carbon atom with unsubstituted, or substituted with 1-3 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, and wherein heteroaryl is a a 5 or 6-membered aromatic ring containing 1, 2, 3 or 4 heteroatoms, independently selected from N, O or S, which is unsubstituted, or substituted with 1 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O) $NH_2$, —$C_1$-$C_6$ alkylC(O)$NH_2$, or —$C_1$-$C_6$ alkylOC(O)$NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, or aryl.

2. A compound of claim 1, wherein $R^1$ is selected from the group consisting of
1) —$ONO_2$,
2) —O—$CH_3$,
3) —O-aryl,
4) —O-heteroaryl,
5) —O—$C_{3-8}$ cycloalkyl, and
6) halogen,
or a pharmaceutically acceptable salt thereof.

3. A compound of claim 1, wherein Y is selected from the group consisting of —C(O)O$R^2$, —(CH$_2$)$_{1-2}$OH, —OH,

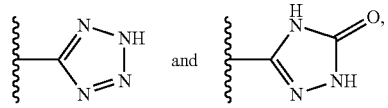 [SMILES: *c1nn[nH]n1 ; *c1n[nH]c(=O)[nH]1]

or a pharmaceutically acceptable salt thereof.

4. A compound of claim 1, wherein $R^1$ is selected from the group consisting of —OCH$_3$, —ONO$_2$, and F, or a pharmaceutically acceptable salt thereof.

5. A compound of claim 4, wherein $R^1$ is —OCH$_3$, or a pharmaceutically acceptable salt thereof.

6. A compound of claim 1, wherein Y is —C(O)OH or —C(O)OCH$_3$ and $R^1$ is —O-CH$_3$, or a pharmaceutically acceptable salt thereof.

7. A compound of claim 1, wherein Y is —C(O)OH or —C(O)OCH$_3$, or a pharmaceutically acceptable salt thereof.

8. A compound of claim 1, wherein, R$^5$ and R$^6$ are hydrogen, and x is 1, and z is 0, or a pharmaceutically acceptable salt thereof.

9. A compound of claim 1, wherein the compound is of the formula

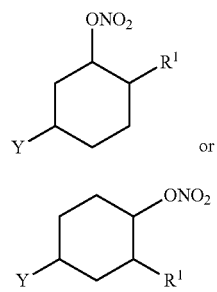

or a pharmaceutically acceptable salt thereof.

10. A compound of claim 1 selected from the group consisting of (1S,3R,4R)-methyl 4-methoxy-3-(nitrooxy)cyclohexanecarboxylate,
(1S,3R,4R)-methyl 3-methoxy-4-(nitrooxy)cyclohexanecarboxylate,
(1S,3R,4R)-methyl 3-methoxy-4-(nitrooxy)cyclohexanecarboxylate,
(1S,3S,4S)-methyl 4-methoxy-3-(nitrooxy)cyclohexanecarboxylate,
(1R,3S,4S)-methyl 4-methoxy-3-(nitrooxy)cyclohexanecarboxylate,
(1R,3R,4R)-methyl 3-methoxy-4-(nitrooxy)cyclohexanecarboxylate,
(1R,3S,4S)-methyl 3-methoxy-4-(nitrooxy)cyclohexanecarboxylate, and
(1R,3R,4R)-methyl 4-methoxy-3-(nitrooxy)cyclohexanecarboxylate, or a pharmaceutically acceptable salt thereof.

11. A pharmaceutical composition comprising a compound of claim 1 and a pharmaceutically acceptable carrier.

12. A method for treating hypertension in a patient which comprises administering to the patient a therapeutically effective amount of the composition of claim 11.

* * * * *